US00PP26337P3

(12) United States Plant Patent
Korlipara

(10) Patent No.: US PP26,337 P3
(45) Date of Patent: Jan. 19, 2016

(54) *BERGENIA* PLANT NAMED 'SPRING FLING'

(50) Latin Name: ***Bergenia* hybrid**
Varietal Denomination: Spring Fling

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 118 days.

(21) Appl. No.: 14/120,292

(22) Filed: May 14, 2014

(65) Prior Publication Data

US 2015/0334905 P1 Nov. 19, 2015

(51) Int. Cl.
*A01H 5/00* (2006.01)

(52) U.S. Cl.
USPC ..... Plt./409

(58) Field of Classification Search
USPC ..... Plt./409
See application file for complete search history.

*Primary Examiner* — Annette Para
(74) *Attorney, Agent, or Firm* — Klarquist Sparkman, LLP

(57) ABSTRACT

A new and distinct *Bergenia* plant characterized by numerous inflorescences flowering at about the same height, large, deep pink flowers, clean, shiny and dark red brown winter leaves, and excellent vigor.

1 Drawing Sheet

Botanical denomination: *Bergenia* hybrid.
Variety designation: 'Spring Fling'.

BACKGROUND OF THE INVENTION

The present invention relates to a new and distinct cultivar of *Bergenia* hybrid and given the cultivar name of 'Spring Fling'. *Bergenia* is in the family Saxifragaceae. The new cultivar originated from a planned breeding program to create outstanding garden *Bergenia*. The new cultivar was created from controlled crosses using proprietary parents. The exact parents were not recorded and are unknown.

SUMMARY OF THE INVENTION

This new *Bergenia* is unique in having:

1. numerous inflorescences flowering at about the same height,
2. large, deep pink flowers,
3. clean, shiny and dark red brown winter leaves, and
4. excellent vigor.

Compared to *Bergenia* 'Bressingham Ruby', U.S. Plant Pat. No. 7,344, the new cultivar has larger flowers, smaller leaves, more crowns and more flowering stems with shorter flower stalks.

Compared to *Bergenia* 'Rotblum', an unpatented plant, has larger flowers, smaller leaves, more crowns and more flowering stems that are more upright.

This new cultivar has been reproduced only by asexual propagation (division and tissue culture). Each of the progeny exhibits identical characteristics to the original plant. Asexual propagation by tissue culture using standard micropropagation techniques with terminal shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a 9 month old *Bergenia* 'Spring Fling' in February in the trial gardens in Canby, Oreg.

FIG. 2 shows the same plant in late April.

DETAILED PLANT DESCRIPTION

The following is a detailed description of the new *Bergenia* based on observations of nine-month-old specimens grown in the ground in full sun in the trial fields in late April in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Type.*—Herbaceous perennial.
*Hardiness.*—USDA Zones 3 to 9.
*Size.*—51 cm wide and 34 cm tall without flowers, 44 cm tall with flowers.
*Form.*—Clumping.
*# Crowns.*—About 50.
*Vigor.*—Excellent.
*Roots.*—Fibrous network, White 155A.

Leaf:

*Arrangement.*—Rosette.
*Number.*—About 8 per rosette.
*Type.*—Simple.
*Shape.*—Obovate.
*Blade size.*—Grows to 17 cm long and 10.5 cm wide.
*Margins.*—Denticulate.
*Apex.*—Obtuse.
*Base.*—Attenuate.
*Venation.*—Pinnate.

*Surface texture.*—Glabrous on both surfaces.

*Petiole description.*—Grows to 20 cm long and 2.5 cm wide, glabrous, base sheathing, sheath ligulate and spreading to 2.5 mm wide at base, Yellow Green 145A strongly tinted Greyed Purple 185A in sun.

*Color.*—Late spring and summer topside Green 137A with margin edged Greyed Purple 185A and with main vein and largest lateral veins Yellow Green 145D, bottom side Yellow Green 147B with veins tinted Greyed Purple 185A; winter and early spring leaves topside between Greyed Purple 187A and Brown 200A with largest veins Greyed Purple 185A to Yellow Green 145B where shaded, bottom side Greyed Purple 187B.

Inflorescence:

*Type.*—Scapose cyme.

*Number of cymes.*—About 13.

*Number of flowers per scape.*—To about 80.

*Size of inflorescence.*—Grows to 18 cm long and 14 cm wide.

*Peduncle.*—Grows to 31 cm tall and 12 mm wide, glabrous on bottom half to glandular near top, Yellow Green 145C in shade and Red Purple 185A in sun.

*Pedicel.*—Grows 4 mm to 15 mm long, 1.5 mm wide, glossy and glandular, Greyed Purple 187A.

Flower bud:

*Size.*—7 mm long and 5 mm wide.

*Shape.*—Ovoid.

*Surface.*—Glabrous.

*Color.*—Greyed Purple 185B.

Flower:

*Type.*—Bisexual.

*Size.*—Grows to 20 mm long and 35 mm wide.

*Corolla description.*—Grows to 20 mm long and 35 mm wide, bell-shaped, glabrous inside and out; petals, 5 to 6 in number, grow to 20 mm long and 12 mm wide, orbicular to obovate, margin entire, tip obtuse, base attenuate, glabrous on both sides, topside Red Purple 71A, bottom side 72C.

*Calyx description.*—8 mm long and 9 mm wide, campanulate, 5 lobes each 5 mm long and 3 mm wide, not overlapping, oblong, margin entire, tips obtuse, sparsely glandular outside, glabrous inside, color inside and outside Greyed Purple 185B at base and Brown 200C on lobes.

*Pistil description.*—2 to 3, fused at base, Greyed Red 181A overall, each 11 mm long and 2.5 mm wide, ovary oval, 3 mm long and 2.5 mm wide; style 5 mm long and 1.5 mm wide, stigma 1 to 2 mm wide.

*Stamen description.*—10 in number, mm long, filaments 9 mm long, Red Purple 61A, anthers 1 mm long, Yellow White 158A; pollen White 155A.

*Bloom period.*—April in Canby, Oreg.

*Lastingness of bloom.*—Each flower lasts about a week.

*Fragrance.*—None.

Fruit: None seen.

Seed: None seen.

Pest and diseases: Pest and disease resistance are typical for this type of *Bergenia*. No known resistances.

I claim:

1. A new and distinct *Bergenia* plant as herein illustrated and described.

* * * * *

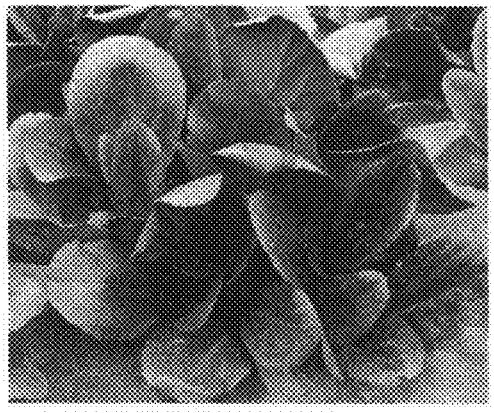
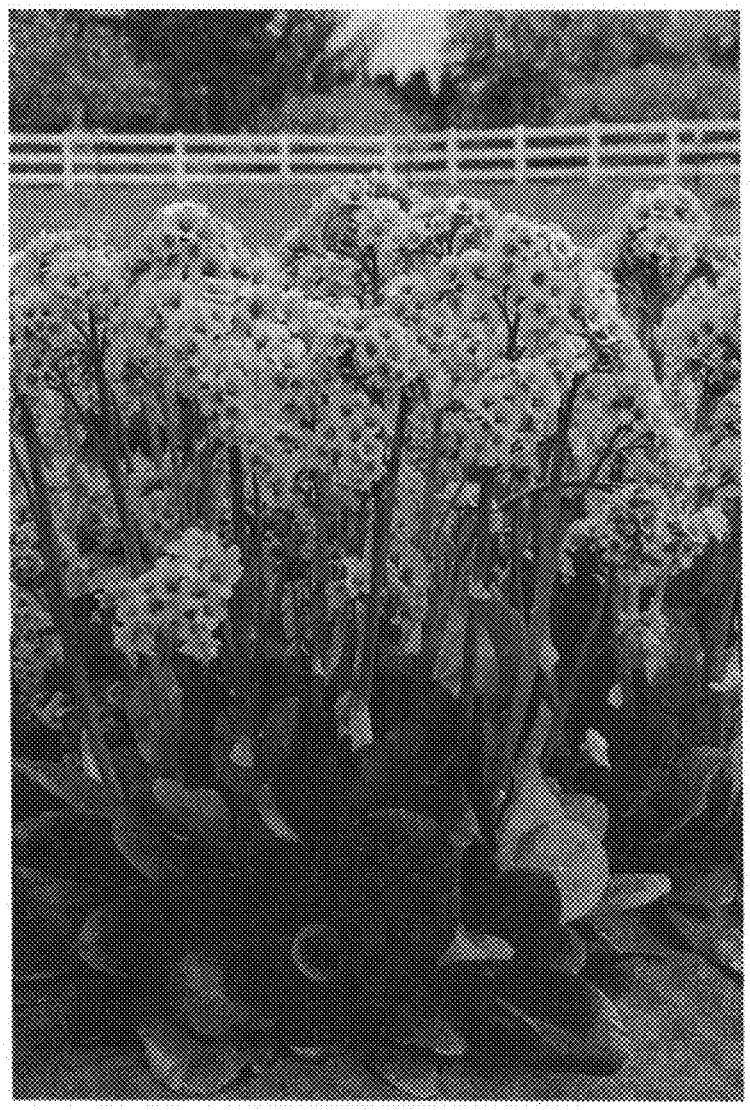

FIG. 1 on right
FIG. 2 below